United States Patent [19]

Goble et al.

[11] Patent Number: 5,713,897

[45] Date of Patent: Feb. 3, 1998

[54] ANTERIOR CRUCIATE LIGAMENT TENSIONING DEVICE AND METHOD FOR ITS USE

[76] Inventors: E. Marlowe Goble, 850 E. 1200 North; David P. Luman; Alan Chervitz, both of 152 S. 600 West, all of Logan, Utah 84321; Brad Story, 38 Chestnut La., Smithfield, Utah 84335; Tim Simon, 12581 Silver Fox Rd., Los Alamitos, Calif. 90720

[21] Appl. No.: 812,487

[22] Filed: Mar. 6, 1997

[51] Int. Cl.⁶ ............................................. A61B 17/56
[52] U.S. Cl. ........................ 606/53; 606/1; 606/55; 606/88
[58] Field of Search ..................... 606/1, 55, 88, 606/53

[56] References Cited

U.S. PATENT DOCUMENTS

| Re. 34,293 | 6/1993 | Goble et al. | 623/13 |
|---|---|---|---|
| 4,301,551 | 11/1981 | Dore et al. | |
| 4,400,833 | 8/1983 | Kurland. | |
| 4,467,478 | 8/1984 | Jurgutis. | |
| 4,590,928 | 5/1986 | Hunt et al. | |
| 4,597,766 | 7/1986 | Hilal et al. | 623/13 |
| 4,605,414 | 8/1986 | Czajka | 623/13 |
| 4,668,233 | 5/1987 | Seedhom et al. | 623/13 |
| 4,712,542 | 12/1987 | Daniel et al. | |
| 4,744,793 | 5/1988 | Parr et al. | 623/13 |
| 4,772,286 | 9/1988 | Goble et al. | 623/13 |
| 4,773,417 | 9/1988 | Moore et al. | |
| 4,834,752 | 5/1989 | Van Kampen | 623/13 |
| 4,870,957 | 10/1989 | Goble et al. | |
| 4,927,421 | 5/1990 | Goble et al. | 606/73 |
| 4,950,270 | 8/1990 | Bowman et al. | 606/72 |
| 4,997,433 | 3/1991 | Goble et al. | 606/64 |
| 5,037,426 | 8/1991 | Goble et al. | 606/96 |
| 5,129,902 | 7/1992 | Goble et al. | 606/65 |
| 5,139,520 | 8/1992 | Rosenberg | 623/13 |
| 5,147,362 | 9/1992 | Goble | 606/72 |

OTHER PUBLICATIONS

"Measure Cruciate Ligament Isometry" by MEDmetric Corporation, San Diego, California, 1988.

*Primary Examiner*—Gary Jackson
*Attorney, Agent, or Firm*—M. Reid Russell

[57] ABSTRACT

An anterior cruciate ligament or soft tissue tensioning and knee displacement measuring device and method for its use to apply a tensile stress into a repaired or replaced graft and to maintain tension on that graft while an interference screw, or like fastener, is turned into a tunnel section end, containing the graft or sutures connected to the graft, wedging it against the tunnel wall, and, during application of the tensile stress, for determining the distance that the knee is displaced. The invention includes a tensioning device having, as a body, a pair of straight rails with a cross member secured across the rails rear or distal ends with forward or proximal rail ends connected to mounting tubes that are for fitting into pins as have been mounted into to extend from a bone cortex, alongside the tunnel section end, and including a trolley maintained to travel between the body rails. The trolley includes a mount arranged to receive and maintain sutures that extend out from the tunnel end, with trolley movement provided by turning a connected rod turned through the cross member to impart a tensile force into the ligament graft, with the amount of the applied force measured by a slide indicator arranged with the trolley. Additionally, the invention includes the knee displacement measuring device for measuring displacement during application of a tensile stress to sutures attached to the ligament graft.

17 Claims, 8 Drawing Sheets

ANTERIOR CRUCIATE LIGAMENT TENSIONING DEVICE AND METHOD FOR ITS USE

BACKGROUND OF THE INVENTION

1. Field of the Invention

This invention relates to devices for use in an arthroscopic surgical procedure performed on a patient's knee to repair or replace their anterior cruciate ligament, and in particular to a device used for setting a measured tension into a ligament whose femoral end is secured in a ligament tunnel.

2. Prior Art

In a practice of an arthroscopic surgical procedure for repair or replacement of an anterior cruciate ligament, it has become a usual practice to form straight tunnel sections that pass through the distal femur and proximal tibia and through the ligament connection sites or points of origin in the knee. The tunnel formation may involve formation of a blind femoral tunnel to receive a connector for endosteally mounting the ligament femoral end. Or another such procedure may involve forming both the tibial and femoral tunnel sections to be open at both bone cortexes. With the knee bent approximately ninety (90) degrees, the tunnel sections form a straight tunnel from the tibial tuberosity into or through the femur. In an installation of a replacement ligament graft that is mounted at its femoral end, or for a ligament graft segment that has been secured onto a section of an original ligament, it has been difficult to reliably set and maintain a measured tension on the ligament as the ligament graft tibial end is secured to the proximal tibia and for verifying that the amount of knee displacement is within limits. The invention provides a device and method for its use to meet these needs for both setting a desired tension in a ligament graft, for measuring knee displacement and for maintaining that tension on the ligament as the graft tibial end is secured to or within the proximal tibia.

One of the inventors has developed a number of cruciate ligament mounting arrangements, for example U.S. Pat. Nos. 4,772,286; 4,870,957; 4,927,421; 4,997,433; 5,129,902; 5,147,362; and U.S. Pat. No. Re. 34,293. Also, several U.S. Pat. Nos. 4,605,414, 4,950,270 and 5,139,520, have shown mounting devices and arrangements for setting ligament tension prior to seating such devices in bone tunnel sections in a cruciate ligament replacement procedure. Also a device known as an Arthrometer, manufactured by MEDmetric Corporation, of San Diego, Calif., has been developed and marketed that has a number of elements in common with the invention but does not provide structure to allow a graft tibial end to be secured to or within the proximal tibia, as does the invention.

Further, a number of devices and procedures have heretofore been employed to secure ligament ends onto a bone surface after application of a tensile force thereto. Several of which are shown in U.S. Pat. Nos. 4,400,833; 4,467,478; 4,590,928; 4,597,766; 4,668,233; 4,773,417; and 4,834,752. None of which arrangements, however, has provided for setting and maintaining a certain tensile stress on a ligament graft as it is mounted within or alongside a tunnel section and additionally provides for measuring knee displacement, as does the device of the invention.

Several ligament mounting arrangements have been developed for mounting in ligament tunnel ends that have provided for turning end connectors of a prosthetic ligament, as shown in U.S. Pat. Nos. 4,301,551 and 4,744,793. None of which devices, however, has provided for applying and maintaining a measured tensile force to the ligament graft and for determining knee displacement as does the arrangement of the invention.

A patent to one of the inventors, U.S. Pat. No. 5,037,426 and another patent to Daniel, et al., U.S. Pat. No. 4,712,542, both show apparatus and procedures for their use for measuring a tensile force as applied to a ligament. Neither of these patents, however, provides for conveniently setting and maintaining an applied tensile force on the ligament graft and for measuring knee displacement as the ligament is being secured to the proximal tibia. Further, the cited earlier devices and procedures for their use, as set out above, are structurally and functionally unlike the device of the present invention.

SUMMARY OF THE INVENTION

It is a principal object of the present invention to provide an anterior cruciate ligament tensioning device and system for its use in an arthroscopic surgical procedure for repair or replacement of a patient's anterior cruciate ligament that provides for both setting a required tensile stress on a cruciate ligament graft maintained in a femoral tunnel section, and for maintaining that applied tensile force as the ligament end is mounted in or onto the proximal tibia.

Another object of the present invention is to provide a device and method for its use that can be easily and securely attached to a patient's tibial tuberosity to provide align of a movable rod, post, or the like, thereof, with the end of a tibial tunnel, with the movable rod receive the ligament graft end, or ends of a suture or sutures that have been attached to the ligament graft end, and for releasably securing the graft end, suture or sutures to the vertical rod, that moved so as to apply a measured tension into the ligament as read from a gauge of the device.

Still another object of the invention is to provide a device that can, while measuring ligament graft tension, can be further determine knee displacement utilizing a knee displacement measuring device of the invention.

Still another object of the present invention is to provide a device and procedure for its use in an anterior cruciate ligament repair procedure for quickly and reliably setting and maintaining a desired tensile stress in a ligament graft and for measuring knee displacement with the ligament is maintained under tension, which device can be easily installed onto and removed from the patient's tibial tuberosity and, with the ligament graft maintained under tension, allows access to the tibial tunnel end.

To utilize the device of the invention, with the patient's skin opened to expose the tibial tunnel cortex end at the tibial tuberosity and the cortex surface adjacent thereto, a pair of straight parallel pins are fitted into the tibial cortex, preferably through a jig. Which pins are to serve as guides to fit into slide sleeves of the device providing for aligning and mounting the invention. The sleeves extend parallel from a forward or proximal end of the device body, and fit to a U-shaped craddle arranged across open ends thereof. The craddle is to fit against the tibia cortex, adjacent to but spaced apart from the tibial tunnel end. With a femoral end of the ligament graft secured in the distal femur tunnel, the ligament graft tibial end, or a suture or sutures that are attached to that ligament graft at a tibial end, extend out of the tibial tunnel end and are passed across the U-shaped craddle end.

The device body, from the forward ends of the U-shaped craddle, includes a pair of spaced parallel rails wherebetween a trolley is arranged to travel back and forth. A forward end of the trolley includes a vertical post as a ligament or suture mount, which post is at a right angle to and is approximately parallel to the body craddle end. The vertical post is arranged to receive and have wound therearound the ligament graft tibial end or sutures connecting to the ligament graft, as have passed across the craddle end of the device. The trolley is arranged to side on opposing surfaces of the spaced parallel rails. Trolley movement along the rails is provided by movement of a threaded rod that extends from a trolley distal end that is fitted through a rear cross beam of the device body that is secured across the rails. Which threaded rod includes a nut that, when manually turned thereon, turns the threaded rod to move the trolley towards the rear cross beam. With a ligament graft that is attached to the vertical post, trolley movement places the ligament graft under a tensile stress.

For applying and measuring the tension applied to the ligament graft, a slide is arranged in a longitudinal slot formed in the trolley that is spring biased towards a top or proximal trolley end by a coil spring wherethrough the threaded rod is fitted. The threaded rod, at a forward face of the rear cross beam, is turned through an end collar. As a tensile force is applied to ligament graft end or suture end through a turning of the nut by an operator, that force is both applied at and is reflected by travel of the slide along the trolley longitudinal slot. The edge or edges or which slot include spaced markings scribed at intervals therealong for comparison with the position of the slide for determining the applied tensile force.

In practice, with the device sleeves fitted onto the pins that have been mounted in the tibial cortex, a desired spacing distance of the device U-shaped craddle end to the tibial cortex surface is provided by a turning of positioning bolts into threaded distal ends of the device sleeves. The ends of the positioning bolts to engage the pin ends, providing a rigid mounting of the device onto the tibial tuberosity. Thereat, a tibial end of the ligament graft, whose femoral end is secured in the femur endosteum or onto the femur cortex, or to an end portion or portions of sutures that are secured to a ligament graft located within a tunnel section, are passed across the U-shaped craddle device end. The ligament graft end of attached sutures are stretched to and wound around the trolley vertical post. Thereafter, by a manual turning of the nut onto the threaded rod to a slide maintained in a longitudinal slot of the trolley is moved towards the cross beam rear end, applying a tensile stress to the ligament graft. The slide is moved within the trolley slot from a zero, or a no stress position that is at the top or proximal end of the slot, to a position along the slot. Which slide position along the slot is indicative of the force in pounds being applied. Slide positioning is compared with spaced marking scribed along the slot edge or edges that correspond to the applied stress, preferably measured in pounds.

Additionally, the device of the invention may include a knee displacement measuring device for mounting onto a brace that spans between and is secured above the slide sleeves. From which brace, a vertical segment extends upwardly from the brace center for receiving the measuring device releasably mounted thereto. The measuring device of the invention includes a rack and pinion arrangement consisting of a straight rod as the rack that has had teeth formed along a mid-section thereof that is fitted to slide through ends of a straight body. The pinion is a pinion gear whose teeth are fitted to mesh with the rod teeth and is mounted to turn on an axle that is journaled in the body of the displacement measuring device and includes a pointer maintained to one axle end. The pointer, when turned, is to travel over a scale scribed on a dial secured to the body measuring device that has increments of distance scribed at spaced intervals therearound. In practice, the straight rod can be fitted through the body ends to turn a threaded forward rod end into a hole formed into the patient's patella, whereat the pointer is set to zero. Thereafter, when a tension is applied to the ligament graft, the patella will be displaced, thereby pulling the rod through the measuring device body to turn the gear and axially connected pointer. Pointer positioning over a scale marking indicates the distance the patella has been displaced and is measured in centimeters.

With a desired tensile stress applied to the ligament graft, the end of the tibial tunnel is unobstructed an a tibial graft end thereof can be secured in the tibial tunnel as by turning an interference screw therein, or other by another appropriate mounting. Whereafter the ligament graft end, suture or sutures can be released from the tensioning device of the invention, and the straight rod turned out of the patella.

DESCRIPTION OF THE DRAWINGS

In the drawings that illustrate that which is presently regarded as the best mode for carrying out the invention.

DETAILED DESCRIPTION OF THE INVENTION

Figure 1:
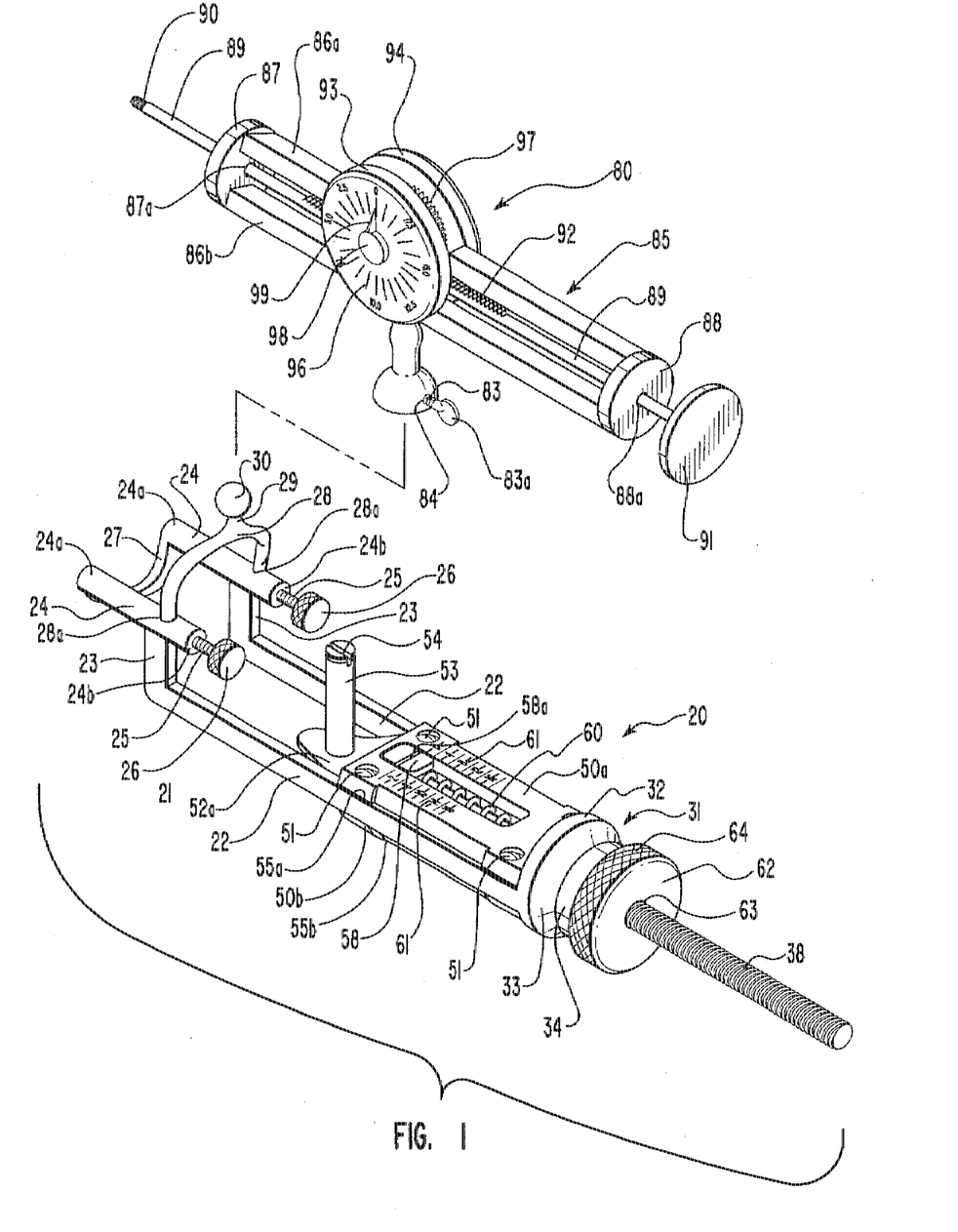
FIG. 1 is a profile perspective view of an anterior cruciate ligament tensioning device of the invention showing also a knee displacement measuring device of the invention aligned for mounting to the ligament tensioning device.
Figure 2:
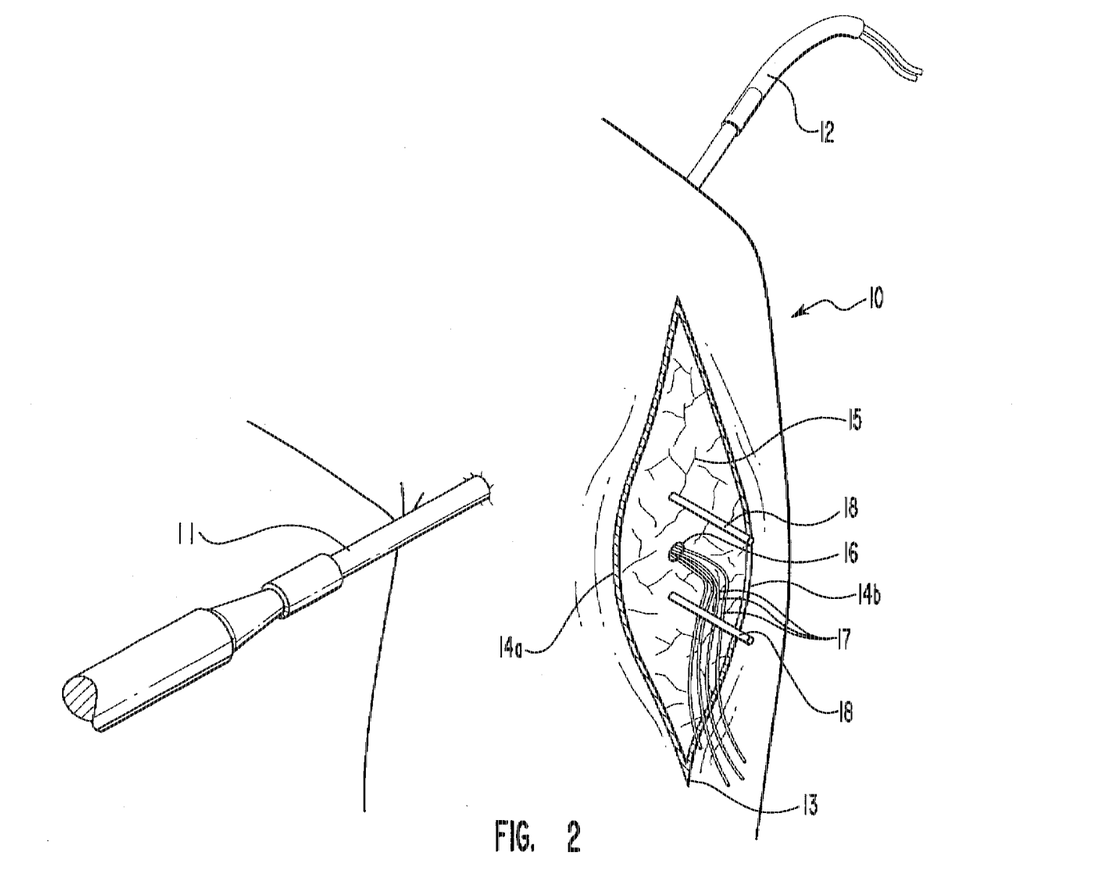
FIG. 2 is frontal perspective view of a patient's knee showing instruments used in an arthroscopic surgical procedure inserted into the sides of the knee, with a longitudinal incision having been made into the knee to expose the tibial tuberosity and the skin shown folded back to expose a cortex end of a tibial tunnel section, showing a pair of parallel straight pins installed in the tibia cortex alongside and equally spaced apart from the tibial tunnel end, and with a number of suture strands shown extending out of the tibial tunnel end.
Figure 2A:
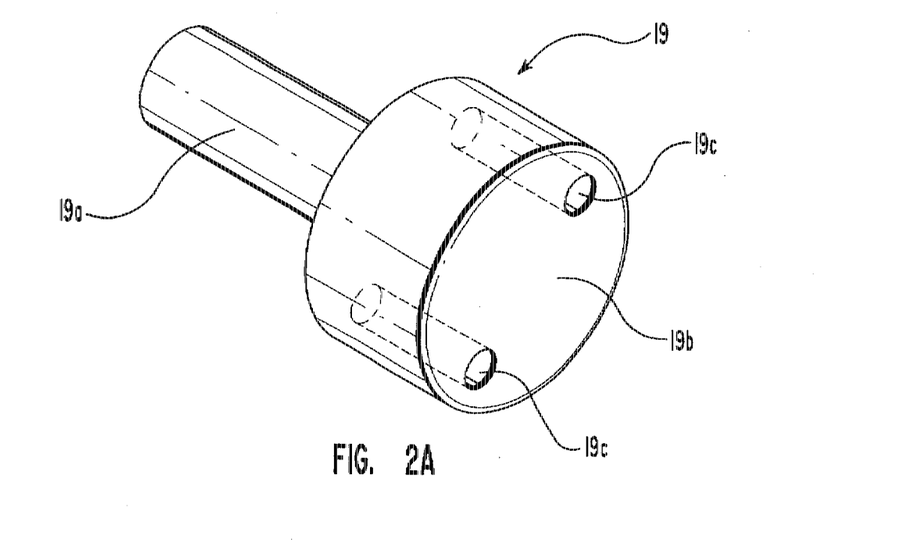
FIG. 2A is a profile perspective view of a jig having a sleeve for fitting into the tibial tunnel section whereto is mounted a short cylinder or disk that includes a pair of holes formed therethrough that are for guiding drilling of holes into the proximal tibia to receive the straight pens of FIG. 2 turned therein.

FIG. 1 shows an anterior cruciate ligament tension device 20 of the invention, hereinafter referred to as device. The device 20 is for use in an arthroscopic surgical procedure practiced on a patient's knee 10. The procedure, as illustrated in FIG. 2, involves a surgeon, not shown, inserting arthroscopic surgical tools 11 and 12, or the like, through ports formed into knee 10 in between the distal femur and proximal tibia surfaces. The device 20 is used to apply a measured tension into an anterior cruciate ligament graft and may include, for operation therewith, a knee displacement measuring device 80, that is mounted onto device 20 for measuring knee displacement at the patella in a ligament replacement procedure.

Figure 8:
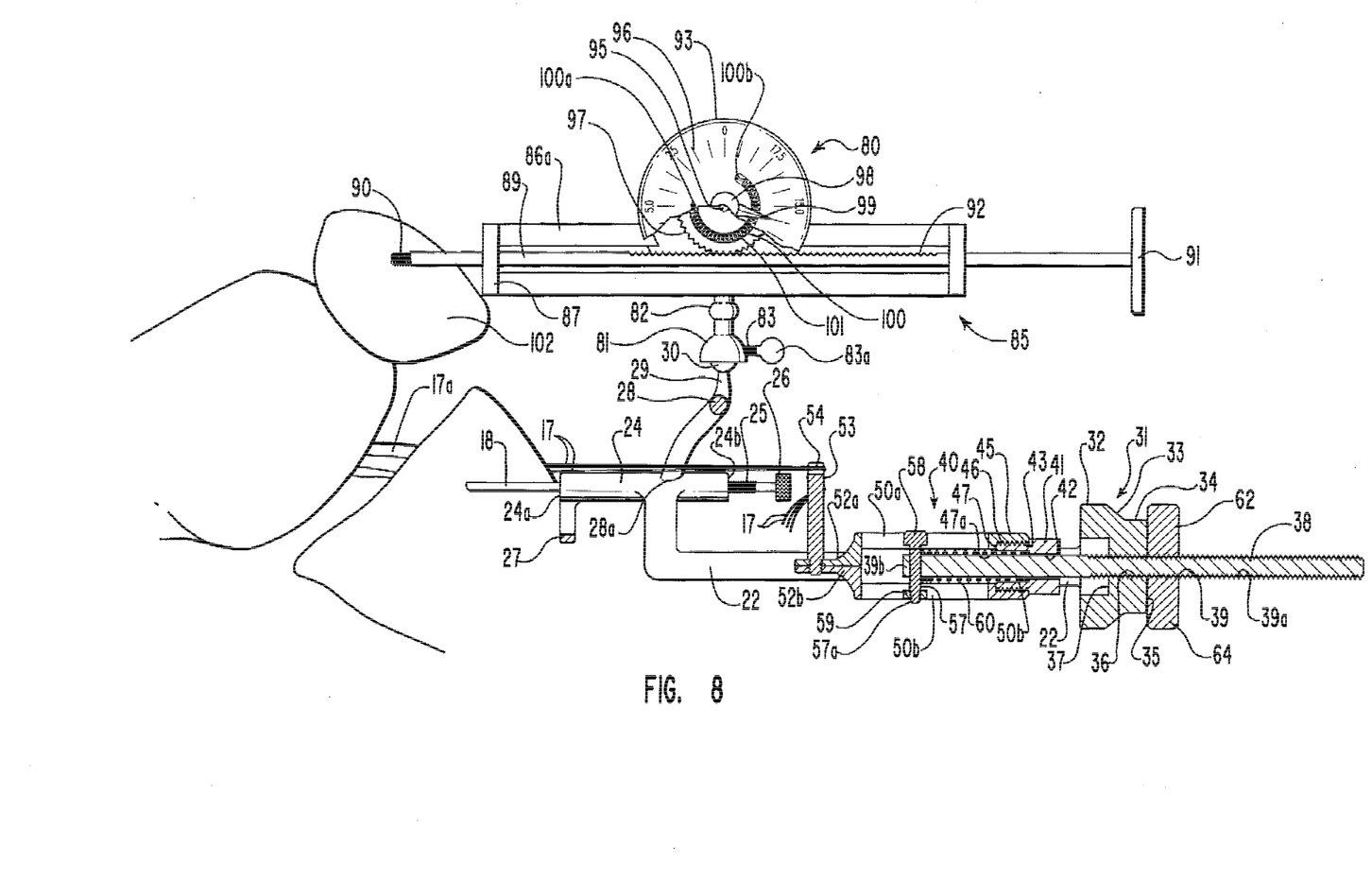
FIG. 8 is a view like FIGS. 1, 3 and 4, except that the straight pins have been aligned across the tibial tuberosity, and showing the knee displacement measuring device mounted between the ligament tension device and patella to measure knee displacement.

The surgical procedure involves forming tibial and femoral tunnel sections through the opposing points of ligament origin on the distal femur and proximal tibia. An end 16 of the tibial tunnel section is shown in FIG. 2 formed through the cortex of the tibial tuberosity 15, wherethrough a plurality of suture strands 17 are shown extending. The suture stands 17 connect onto a tibial end of a ligament graft 17a, as shown in FIG. 8, that is securely mounted to extend through the femoral tunnel section, across the knee, and into the tibial tunnel section. So arranged, a tensile stress can be applied to stretch the ligament graft across the patient's knee 10, as shown in FIG. 8, by pulling on the sutures 17.

Figure 3:
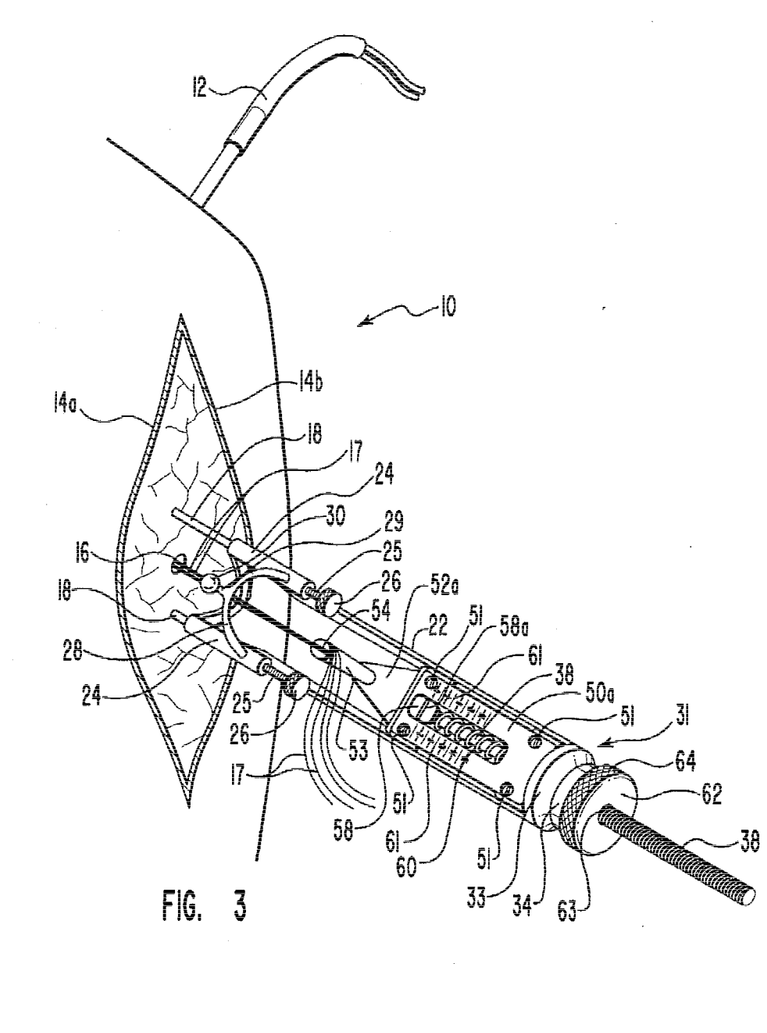
FIG. 3 shows the device of FIG. 1 installed onto the parallel pins of FIG. 2 and showing the suture strands fitted over and wrapped around a vertical post of a trolley of the device.
Figure 3A:
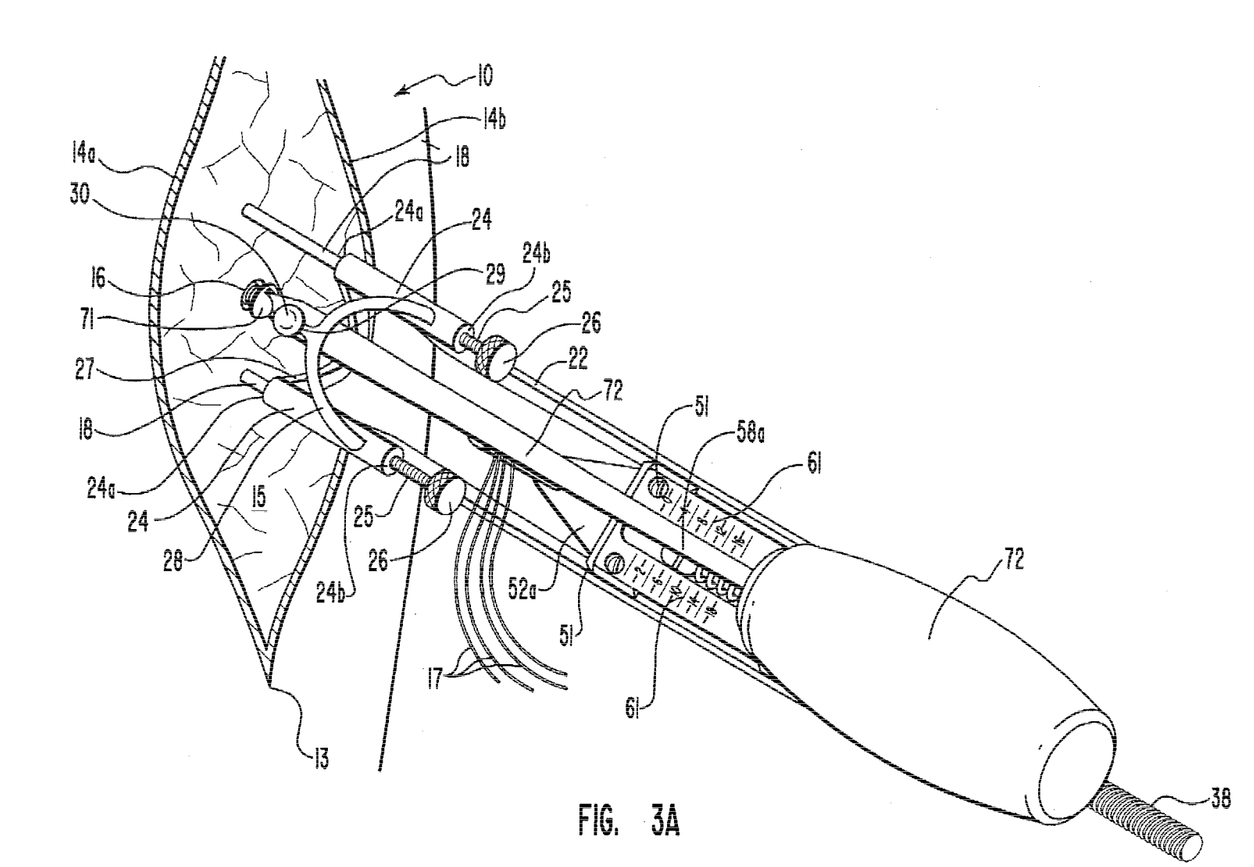
FIG. 3A is a view like FIG. 3 additionally showing a screw driver mounting a screw for turning into the tibial tunnel section end alongside an end portion of a ligament graft under tension, for securing that graft end in the tunnel section.
Figure 4:
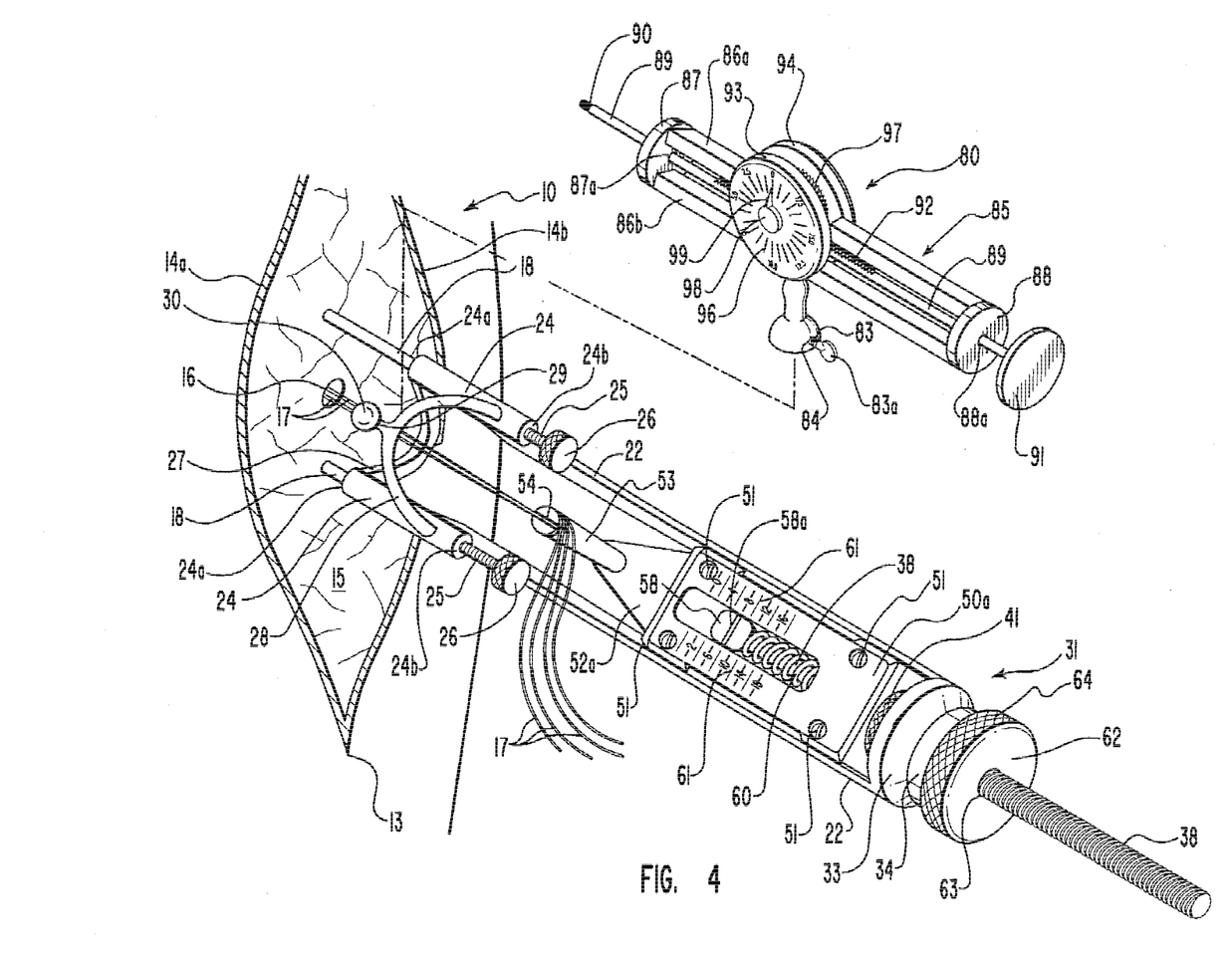
FIG. 4 is an enlarged view of the tibial tuberosity and device of FIG. 3, showing the trolley as having moved towards the device distal end with a slide shown arranged to travel along a longitudinal slot formed in the trolley, with the slide shown as having moved to a location where a lateral marking thereon has aligned with one of a series of spaced markings scribed along the longitudinal slot edges identified with numbers and showing the knee displacement measuring device aligned for mounting thereto.
Figures 5, 6:
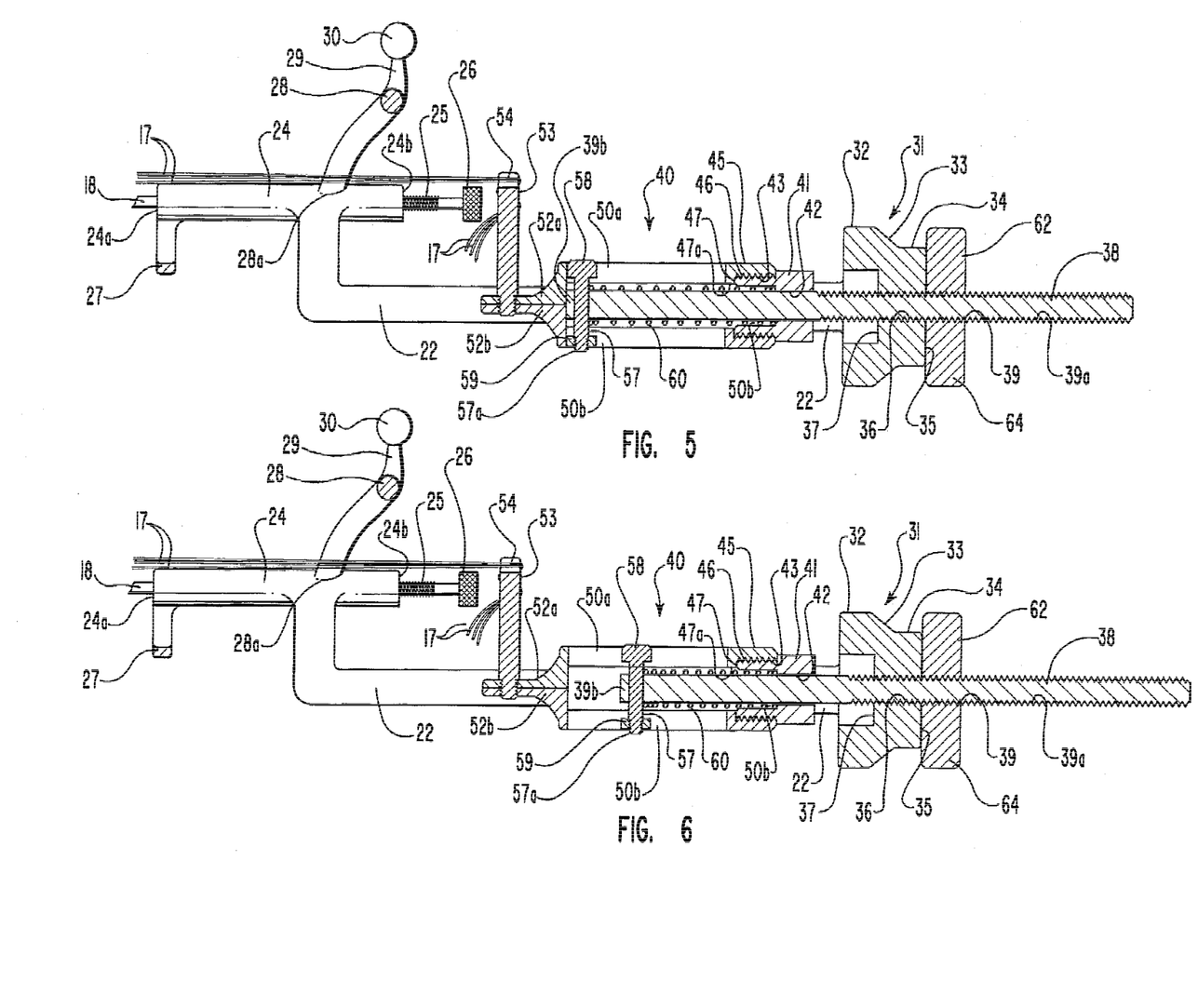
FIG. 5 is a side elevation longitudinal sectional view of the device of FIG. 1 including the suture strands in FIG. 3, showing the slide as being at the top or proximal end of the trolley longitudinal slot prior to application of a tensile stress to the sutures.
FIG. 6, is a view like that of FIG. 5 only showing the slide as having moved to the attitude shown in FIG. 4 indicating that a tensile stress has been applied to the suture strands.

The device 20 provides for stretching the ligament graft 17a by application of a desired tensile stress thereto and provides for maintaining that applied stress to allow the tibial ligament graft end to be secured within the tibial tunnel end. Which ligament graft end mounting is preferably provided by turning an interference screw between the graft and tunnel wall, as shown in FIG. 3A, or can be formed as by turning a set screw through the tibia to intersect the ligament graft end, not shown, or a like procedure could be so employed within the scope of this disclosure. To provide for releasably mounting the device 20 to the tibial cortex, as shown in FIG. 2, a longitudinal incision 13 is made in the proximal tibial and the edges 14 of that incision are laid or folded back, to expose the tibia cortex surface 15 and tibial tunnel end 16. A pair of spaced apart parallel pins 18 are turned, driven, or otherwise fitted into the cortex surface adjacent to and are equally spaced apart from the tunnel end 16. A jig 19 is provided for guiding drilling of holes to receive properly spaced apart pins 18. The jig 19 includes a sleeve 19a that is for inserted into the tibial tunnel section end 16 to where an undersurface of a guide disk 19b, that is maintained across an upper end of sleeve 19a, contacts the tibial cortex. The guide disk 19b, as shown, includes a pair of drilling holes 19c that are spaced equidistantly from the sleeve longitudinal center, and wherethrough a drill is passed to form holes into the tibial tuberosity that are to receive pins 18 therein. The pins 18 are for receiving the device 20 fitted thereon, as shown in FIGS. 3 and 4, and can be aligned in a vertical axis through the tibial tunnel end 16, or can be aligned in a horizontal axis, as shown in FIGS. 5, 6 and 8.

In FIG. 1 the device 20 is shown to include a body 21 that is essentially a frame that has as sides straight equally spaced apart longitudinal rails 22 that are each upturned at right angles as forward or proximal ends 23 and mount, sleeves 24 secured across top ends thereof. So arranged, sleeves 24 are parallel to one another and are open longitudinally therethrough. The sleeve opening in a forward or proximal end 24a is smooth walled, for the sleeve to slide freely onto one of the pins 18, as shown in FIGS. 3, 4, 5, 6 and 8, and accordingly sleeves 24 and pins 18 are spaced the same distance apart. The pins 18, each slide into the sleeves 24, to where the pin head end contacts and end of a bolt 25 that has been turned into a threaded section of the sleeve longitudinal openings that is formed the sleeve rear or distal end 24b. The individual bolts 25 are turned manually into each sleeve 24 by a turning of broad head ends 26 thereof.

The device 20, as set out above, is for fitting onto the pins 18, with the pin 18 head ends making a metal to metal contact with bolt 25 end, forming a metal to metal contact therebetween. In which mounting, the tibial tunnel end 16 will be open across a craddle 27 that is preferably a solid metal section with a downwardly bowed center portion and aligned ends. The craddle ends are connected, at essentially right angles, to opposing surfaces of the sleeves 24, back from the forward or proximal ends 24a thereof, as shown best in FIGS. 5, 6 and 8. So arranged, the as sutures 17 are passed across the middle of craddle 27 to be releasable attached to a vertical post 53, as by winding them therearound, with as shown, the vertical post 53 mounted at a right angle to extend upwardly from a forward or proximal tongue end 52a of a trolley 40, as set out hereinbelow. As shown, a flat U-shaped bar 28 spans between the sleeves 24, connecting at right angles on its ends 28a to sleeves to extend upwardly therefrom. The U-shaped bar 28 includes a straight leg 29, that extends vertically upwardly at a right angle, from the U-shaped bar center. The end of leg 29 includes a ball end 30 secured thereto that is for receiving a knee displacement measuring device 80, as set out below, and which ball 30 also can be held by a surgeon for guiding the sleeve 24 ends onto pins 18.

The straight rails 22 extend parallel to one another and terminate in opposite sides of a rear or distal end cross member here identified as a crown 31. The distal end crown 31 is shown as being tapered at 33 from a greater diameter section 32 to a lesser diameter rear end 34 section and has a flat forward face 35 whereto the straight rails are secured at right angles thereto. A center threaded hole 36 is formed in the crown 31, as shown best in FIGS. 5, 6, and 8, and a cavity 37 is formed in the flat forward face 35. A rod 38 having a threaded rear section 39a, is turned through the center threaded hole 36 to pass through a smooth walled opening 42 of a distal end cap 41 of a trolley 40. The rod forward section 39b is smooth walled. The trolley distal end cap 41, as shown, is arranged to fit into the cavity 37 that has been formed in the flat forward face 35 of distal end crown 31.

The trolley 40, shown in FIGS. 1, 5, 6 and 8, and includes the distal end cap 41 across on its distal end. The distal end cap 41 is stepped inwardly from a midsection, into a threaded cylinder 43. Further, as shown, within the distal end cap smooth walled opening 42, at its forward or proximal end, the opening is stepped outwardly to provide an enlarged opening portion 44. This enlarged opening portion functions as a seat to receive a rear end of a coil spring 60, as set out and discussed hereinbelow.

The trolley 40, as shown best in FIGS. 5, 6 and 8, includes a rear or distal end 45 wherein is formed a threaded longitudinal passage 46 that receives the distal end cap threaded cylinder 43 turned therein to engage an end wall 47. End wall 47, in turn, includes an end segment 47a that, as shown, is a smooth wall passage that receives the distal end cap 41 turned therein. The end segment 47a surface, in turn, aligns with the wall of the enlarged opening 44 for receiving, as set out above, the rear end of the coil spring 60 fitted therein. The trolley 40, shown in FIGS. 1, 5, 6 and 8, is preferably formed to have flat essentially parallel top and bottom sections 50a and 50b that are connected together by fitting screws 51, as shown best in FIGS. 1, 3 and 4. Which screws 51, as shown, are fitted through holes that are formed in the top section 50a four corners. The screws 51 are turned into threaded holes as have been formed in the bottom section 50b, securing the sections together to form trolley 40. In which coupling the top and bottom sections 50a and 50b each include half of the described distal end cap 41, and are joined into a single unit with the threaded cylinder 43 therein. The trolley 40 further includes opposing tongue sections 52a and 52b, that, as shown in FIGS. 5, 6 and 8, extend outwardly as the trolley forward or distal ends. The top tongue section 52a, as shown, mounts the vertical post 53 to extend at a right angle upwardly therefrom. Which vertical post 53, as described above, is to receive the suture strands 17 that are fitted along a slot 54 formed across the post top end, and are wound around the post, as shown best in FIGS. 3 and 4.

The trolley 40, at top section 50a includes a center longitudinal slot 56 wherethrough can be observed the rod 38 smooth forward section 39b, with the coil spring 60 shown fitted therearound. The forward or proximal end of the rod forward section 39b, as shown best in FIGS. 5 and 6, is journaled through a midsection of a slide 57. Which slide 57 is shown as a straight flat section that has a square broad head end 58 whereacross a slot or groove 58a is formed. A lower slide 57 end 57a is shown threaded to receive a nut 59 turned thereover. So arranged the slide 57 is free to travel within the trolley, along slot 54, and away from the slot forward or proximal end. Slid travel occurs when a tensile force is applied to the sutures 17 by turning of a round nut 62 along rod threaded section 39a. The round nut 62 is shown as a flat disk, that is threaded therethrough at 63 and is to receive the rod threaded section 39a to be turned therein to where the nut forward face engages and will act against the end face 35 of the body distal end crown 31, as discussed hereinbelow with respect to the operation of the device 10.

The forward end of the coil spring 60 is fitted against the slide 57 such that, as the rod 38 travels out of the body distal end crown 31, with an operator manually turning a knurled outer surface 64 of the round nut 62, the coil spring 60 will be compressed, tending to resist slide 57 travel. The resistance of coil spring 60 is imparted through the trolley 40 and vertical post 53 into the sutures 17, applying a tensile stress or force into a ligament whereto the sutures 17 are connected. The magnitude of such applied force is reflected in the amount of travel of the slide 57 along the longitudinal slot 56. Slide travel and a resulting applied force, as measured in pounds, is determined by a comparison of the position of a slide 57 a groove 58a formed across a top face or head 58 slot relative to one of markings 61 that have been scribed at spaced intervals along the opposing edges of the longitudinal slot 56.

FIG. 5 shows the device 20 fitted onto pins 18 with the sutures 17 shown passed across the slot 54 of vertical post 53, and wrapped around that post. So arranged, the sutures are drawn tight without a tensile stress having been applied thereto, and the slide head 58 groove 58a, as shown, aligns with a zero scale marking 61, shown in FIGS. 1, 3 and 5. In which attitude, the round nut 62 will not have been turned against the face 35 of the body distal end crown 31. Thereafter, by turning the round nut 62 against the face 35, as shown in FIGS. 4, 6 and 8, the slide 57 journaled onto the end of the smooth section 39b of the rod 38 will be pulled along the longitudinal slot 56. Slide 57 travel aligns the broad head slot or groove 58a with successively larger values of markings 61 as are scribed at spaced intervals along the sides of longitudinal slot 56. FIG. 4 shows the slide broad head groove 58a aligned with a marking identified as eight (8) to indicate that eight (8) pounds of a tensile stress is being applied to the suture 17.

The device 20 is used arranged to maintain an applied force on the sutures as a ligament attachment device, shown as a screw 71 is turned, as by a screw driver 70 shown in FIG. 3A, into tibial tunnel section end 16. The screw 71 to pass alongside and between the ligament graft 17a end and the tunnel section wall so as to secure that ligament graft tibial end in the tibial tunnel section. Without release of the applied tension while a use of an interference screw 71 that is turned into the tunnel section end 16, between the ligament graft end and the tunnel wall, is preferred, alternatively a set screw can be turned through a hole formed in the proximal tibia, not shown, to enter the tibial tunnel section and engage the ligament graft end therein, or other similar ligament graft mounting device or arrangement could also be used within the scope of this disclosure, to lock the suture or a ligament graft end securely in the tibial tunnel section while maintaining an applied tensioning of the ligament graft.

FIGS. 1, 4 and 8, shown the knee displacement measuring device 80 of the invention, that is hereinafter referred to as measuring device 80, aligned for attachment to the ball 30 of device 20, as shown best in FIG. 8. To provide for which attachment, measuring device 80 includes a cup 81 that is secured across a lower end of a post 82. The cup 81 is arranged to fit over the ball 30 and includes turned therethrough utilizing a bolt 83 a wing turning end 83a, or a the like, with the bolt 83 inner end turned through a threaded hole 84 that has been formed through the side of cup 81 to engage and bend against the ball 30.

The measuring device 80, as shown, includes a housing 85 that is formed with straight top and bottom braces 86a and 86b that are secured at right angles to opposing inner and faces of forward and rear flat disk ends 87 and 88, respectively. The forward and rear flat disk ends each include a center opening 87a and 88a, respectively, that are formed therethrough to receive a straight solid rod 89 fitted to slide back and forth. The rod 89 include threads 90 formed along a forward end section and has a disk 91 attachment across its rear end. Further, the rod 89 includes threads 92 formed along its mid-section that are act as a straight rack, functioning as part of a rack and gear combination. Flat front and rear disks 93 and 94, respectively, are secured in parallel to outer surfaces of the top and bottom braces 86a and 86b to span therebetween, and include a center axle 95 therebetween. The forward disk 93, as shown, includes spaced radial marking 96 scribed around the disk with successively greater numbers scribed alongside certain of the marking that are indicative of distances, preferably in centimeters.

Figure 7:
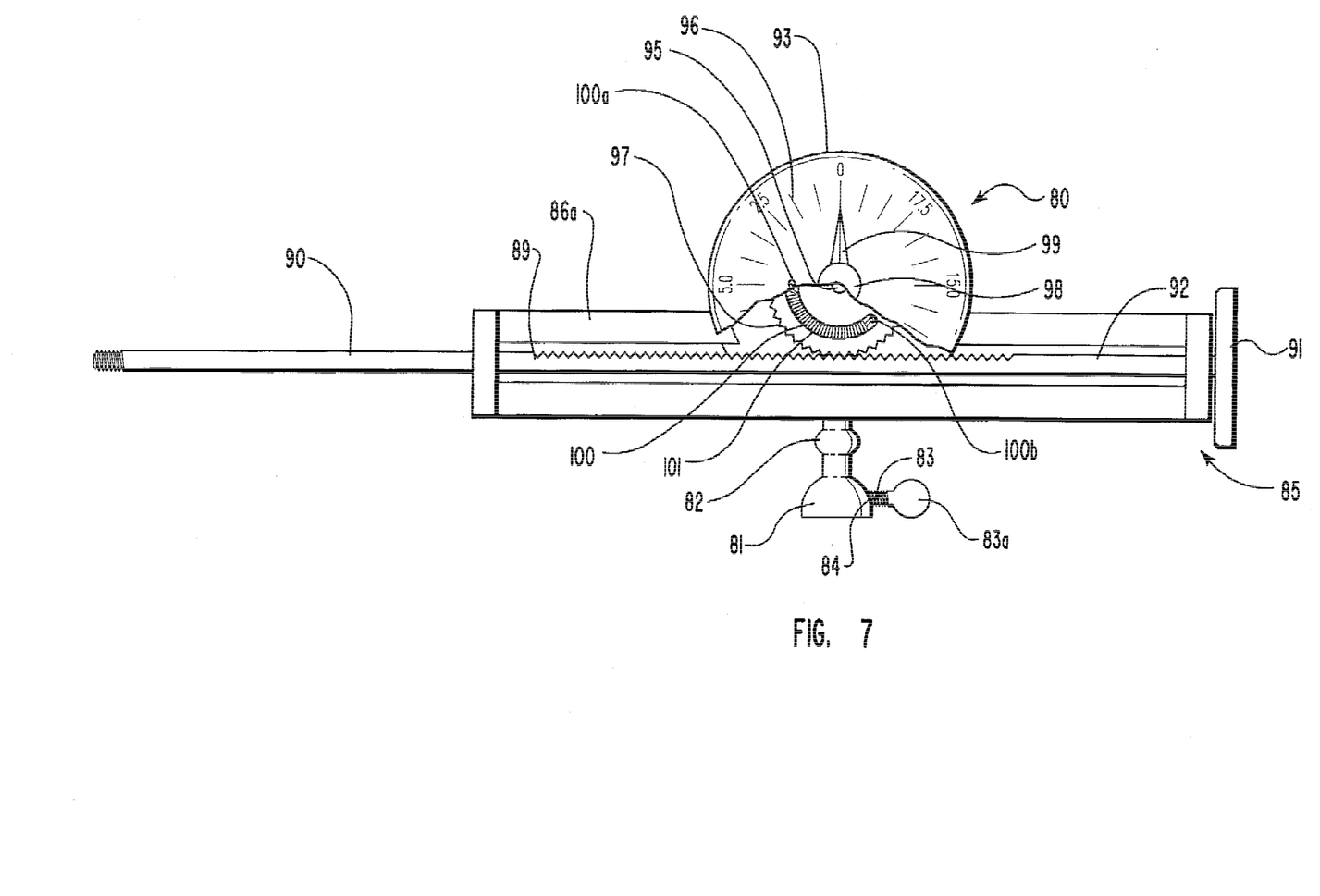
FIG. 7 is a side elevation view of the knee displacement measuring device, showing a section of a dial thereof broken away, to expose a spring biased gear.

The center axle 95, shown in FIGS. 7 and 8, includes a pinion gear 97 of the rack and gear combination that is journaled thereon to be turned by the threads 92 of straight rod 89 pulled along the straight rod is pulled along the gear teeth. The pinion gear 7 is connect to a pointer body 98 having a pointer end 99 that is to travel around the disk, passing over the markings 96, as shown in FIGS. 7 and 8, as the straight rod is moved through the housing 85. So arranged, travel of the straight rod 89, as described below with respect to operation of the measuring device 80, moves the pointer 99 from a zero marking to a numbered marking 96 that is indicative of a distance the straight rod is extended in centimeters. This distance can thereby be used by a surgeon/operator to determine proper ligament graft seating and functioning.

For returning the pointer 99 to a zero position, as shown in FIGS. 1, 4 and 7, a coil spring 100 is maintained in a track 101. The coil spring 100, as shown in FIGS. 7 and 8, is connected at end 100a to the disk 93 and on end 100b to the pinion gear 97. The coil spring 100 is to be stretched along track 101 when the pinion gear 97 is turned, as shown in FIG. 8, and will return to a relaxed state, as shown in FIG. 7, when the threaded end 90 of straight rod 89 is turned out of a patient's patella 102, as illustrated in FIG. 8.

In practice, a surgeon/operator who has formed femoral and tibial tunnel sections in a patient's knee 10, and has secured a femoral end of a ligament graft in the femoral tunnel section, pulls sutures 17 therefrom that are attached to a tibial end of a ligament graft, with sutures passed through the tibial tuberosity tunnel end 16. Pins 18 are then fitted into holes formed in the tibial tuberosity to be adjacent to end 16, preferably utilizing the jig 19. Thereafter, the device 20 sleeves 24 are fitted onto the pins 18, and bolts 25 are turned into the sleeves by tuning head ends 26 thereof to where the bolt ends engage the pin tops, forming a metal to metal contact therebetween. The sutures 17 are then passed across the groove 54 of vertical post 53 and are wrapped around that post to where the sutures 17 are tight but not under tension, as illustrated in FIGS. 3 and 4. The surgeon/operator, to set a desired tension into the sutures and connected ligament graft, first turns the round nut 62 into engagement with the face 35 of the body distal end cap 31. Thereafter, with continued turning, the threaded section 39a of the rod 38 will be turned through the round nut, to pull the slide 57 along the trolley slot 56. The coil spring 60 opposes slide travel and that slide travel applies a tensile stress through the trolley body and vertical post 43 into the sutures 17. This force is read directly off from the device by comparing the positioning of the groove 58a formed across the slide broad head end 58 with the series of markings 61 that have been formed along the edges of the longitudinal slot that is formed in the trolley top section 50a. A marking that the slide groove 58a is aligned indicates to the surgeon/operator the force, in pounds, that is being applied to the suture. When a desired application of tensile stress is achieved, the surgeon/operator, utilizing a selected ligament mounting, such as the set screw 71 shown in FIG. 3A, secures the tibial end of the ligament graft in the tibial tunnel section. Whereafter the tension applied through the device 20 on the sutures 17 is released. The device sleeves 24 can then be pulled off of the pins 18 that themselves can be removed and the incision closed.

Prior to application of a tensile stress through sutures 17, the measuring device 80 can optionally be mounted at cap 81 onto ball 30 for measuring leg displacement during ligament tensioning. The measuring device 80 is operated by pivoting the straight solid rod 89 at disk end 91 to release threads 92 formed therealong out from engagement with the pinion gear 97 threads. This allows the straight rod to be moved through disk ends 87 and 88 holes 87a and 88a, to where threads 90 formed in the straight rod end can be turned into a hole that has been formed into the patient's patella 102. By turning the straight rod threads 97 back into meshing engagement with the pinion gear 97 threads, as the device 80 is operated, the straight rod 89 that is attached to the patella will move with the patella, turning a pointer body 98 around a scale made up of marking 96 scribed as a dial on the face of forward disk 93. A surgeon/operator, comparing the position of the pointer end 99 over a scale marking 96 determines, a distance preferably in centimeters, that the patella has been displaced during ligament tensioning.

While a preferred embodiment of our invention in an anterior cruciate ligament tensioning and knee displacement measuring devices and methods for the use have been shown and described herein, it should be understood that the present disclosure is made by way of example only and that varieties and changes are possible without departing from the subject matter and reasonable equivalency thereof coming within the scope of the following claims, which claims we regard as our invention.

We claim:

1. A soft tissue tensioning device comprising a frame; bone coupling means for rigidly connecting an end of said frame to a bone, adjacent to an opening of a tunnel formed therein; a trolley means arranged for travel along said frame that includes a suture coupling means that aligns with said tunnel opening and is for receiving a suture releasably fitted thereto; a means for moving said trolley along said frame by operation of an adjustment means; and a biasing means for, arranged with said trolley for resisting trolley movement in a direction relative to said frame where a tension is applied through said trolley suture coupling means that is passed into a connected suture or sutures whose other end or ends is attached to a section of soft tissue maintained in said bone tunnel; and means for indicating a tensile force as is being applied to said suture or sutures.

2. A soft tissue tensioning device as recited in claim 1, wherein the suture coupling means is a post secured to extend vertically from the trolley forward or proximal end arranged to receive the suture wound therearound; and the means for moving the trolley is a straight rod having a smooth forward or proximal end for fitting into to turn freely through the frame an in an opening formed in the trolley distal end.

3. A soft tissue tensioning device as recited in claim 1, wherein the frame includes a pair of straight equally spaced rails; and mount means secured to extend across a pair of frame sides that includes a pair of spaced parallel tube means connected to said mount means, to be parallel to said spaced rails that are for fitting over pins extending outwardly for a bone surface adjacent to the bone tunnel end.

4. A soft tissue tensioning device as recited in claim 3, further including a pair of bolt means each for turning into threaded sections of rear portions of each of the pair of sleeves for providing, when turned into said sleeves, for adjusting positioning of the device frame relative to the bone surface.

5. A soft tissue tensioning device as recited in claim 3, further including, with the mount means, a mounting bar secured across the tube means that includes a centered mounting ball means; and a knee displacement measuring device that includes a coupling means for mounting onto said mounting ball means, a body that extends across and at approximately a right angle to said coupling means, and including a straight rod fitted to slide axially therethrough with a proximal end of said straight rod for mounting to a patient's patella, and with a distal end of said straight rod arranged for manual manipulation to project said straight rod patella coupling proximal end out from said body proximal end; and indicator means for measuring a distance said straight rod is projected out from said body.

6. A soft tissue tensioning device, as recited in claim 5, further including a series of teeth formed along a mid portion of the straight rod with said straight rod arranged for turning around its longitudinal axis; a pinion gear means journaled to turn a pointer means over a dial that is secured to said body as the means for measuring, which said pinion gear means teeth are arranged for engaging said straight rod teeth.

7. A soft tissue tensioning device as recited in claim 6, further including means for releasing the pinion gear teeth out of meshing engagement with the straight rod teeth.

8. A soft tissue tensioning device as recited in claim 7, wherein the means for releasing meshing engagement is a disk secured across a rear or distal end of the straight rod rear end that is manually turned to pivot said straight rod teeth out of meshing engagement with said pinion gear teeth; and further including a spring secured on one end to a rear face of the disk and having the other end connected to said pinion gear and said spring is fitted into a track formed in said pinion gear.

9. A soft tissue tensioning device as recited in claim 5, wherein spaced markings are formed on one of the dials whereover the pointed means turns to visually identify increments of distance.

10. A soft tissue tensioning device as recited in claim 1, wherein means for indicating an applied tensile force includes a longitudinal slot formed in a top surface of the trolley means wherein a slide is fitted to travel, which said slide includes an indicator groove formed thereacross, with spaced markings scribed along an edge of said longitudinal slot; and a spring means arranged between said trolley means and an end of the frame.

11. A soft tissue tensioning device as recited in claim 10 wherein the spring means is a coil spring wherethrough a straight rod is fitted with one end of said coil spring to engage the slide and the other said coil spring end to engage a member that is secured across the frame rear or distal end.

12. A soft tissue tensioning device as recited in claim 1, further including a jig that includes a sleeve for fitting into a bone tunnel end, that includes a guide means secured across said sleeve with a pair or space apart holes formed therethrough that are for guiding drilling of a pair of holes into the bone to receive the pins means turned therein.

13. A method for applying, and maintaining tensioning on an end of a section of soft tissue whose opposite end is secured in a bone tunnel during soft tissue end mounting, including the steps of, securing an end of a section of soft tissue in a bone tunnel and securing said soft tissue opposite end to an end or ends of a suture or sutures that extend out from an end of said bone tunnel; securing guide means to the patient's tibia for receiving a tensioning device mounted thereto to where a movable section of said tensioning device is opposite to said bone tunnel end; releasably mounting said suture or sutures to said movable section of said tensioning device; moving said movable section away from said bone tunnel end to stretch said soft tissue section; measuring the applied stretching force; and, with said section of soft tissue under tension, fitting a mounting device into said bone tunnel end to wedge said suture or sutures against said bone tunnel wall.

14. A method as recited in claim 13, wherein the tensioning device includes a body having a pair or parallel rails that mount each mount sleeve to extend forward therefrom that is open for fitting into a pin that has been turned into the bone surface as the guide means for mounting the tensioning device; and a trolley is arranged to travel between said parallel rails that includes an upright post for receiving the suture or sutures wound therearound.

15. A method as recited in claim 14, wherein the trolley is moved along the parallel rails, against a spring biasing, by turning a straight shaft that is fitted through a cross members that extends between said parallel rails, and includes a slide that is maintained to travel along a longitudinal slot that is formed in a face of said trolley that includes spaced markings scribed at spaced intervals along an edge of said longitudinal slot with slide positioning relative to said spaced marking visually, indicating a force as is being applied by said tensioning device.

16. A method as recited in claim 14, further including, utilizing a jig having a sleeve end for fitting into the tibial tunnel end and a disk secured across that sleeve that includes a pair of holes formed therethrough that are equidistant from the center of said sleeve, forming a pair of holes into the bone to receive each of the pair of pins therein for receiving the sleeves fitted thereon.

17. A method as recited in claim 13, attaching a knee displacement measuring device onto the tensioning device, which said displacement measuring device includes a body wherethrough a straight rod is axially fitted having one end for mounting into a patient's patella, and can be axially rotated, and arrangement for visually displaying a distance said straight rod is projected outwardly from said body when a tension is applied into the suture or sutures by operation of the tensioning device.

* * * * *